(12) United States Patent
Park

(10) Patent No.: US 7,609,375 B2
(45) Date of Patent: Oct. 27, 2009

(54) OPTICAL CAVITY FOR GAS SENSOR

(75) Inventor: Jeong-Ik Park, Seoul (KR)

(73) Assignee: ELT Inc., Geumchon-Gu, Seoul (KR)

( * ) Notice: Subject to any disclaimer, the term of this patent is extended or adjusted under 35 U.S.C. 154(b) by 129 days.

(21) Appl. No.: 11/922,343

(22) PCT Filed: Jun. 16, 2006

(86) PCT No.: PCT/KR2006/002315

§ 371 (c)(1),
(2), (4) Date: Dec. 17, 2007

(87) PCT Pub. No.: WO2006/135212

PCT Pub. Date: Dec. 21, 2006

(65) Prior Publication Data

US 2009/0135415 A1    May 28, 2009

(30) Foreign Application Priority Data

Jun. 16, 2005    (KR) .................... 10-2005-0051687

(51) Int. Cl.
*G01N 1/10*    (2006.01)
*G01N 21/00*    (2006.01)
*G01J 5/02*    (2006.01)

(52) U.S. Cl. ................ 356/246; 356/437; 356/440; 250/339.13

(58) Field of Classification Search ............. None
See application file for complete search history.

(56) References Cited

U.S. PATENT DOCUMENTS 7,449,694 B2 *    11/2008    Yi et al. .............. 250/339.13

* cited by examiner

*Primary Examiner*—L. G. Lauchman
*Assistant Examiner*—Amanda H Merlino
(74) *Attorney, Agent, or Firm*—G W i P S

(57) ABSTRACT

An optical cavity for a Non-Dispersive Infrared gas sensor has invented comprising two oppositely arranged parabolic mirrors having common focus located on the common optical axis of the parabolic mirrors, and a plane mirror arranged along the optical axis between the vertex of each of the parabolic mirrors. The NDIR gas sensor has an extended optical path to increase precision and accuracy in the measurement, and substantially increased ventilation opening size to facilitate in and out of the target gas through the optical cavity thereby decreasing the response time required for measuring the gas concentration. The sensors based on the principal of Non-Dispersive Infrared Detection is used the light-absorbing characteristic of gases to measure the amount of light absorption that occur at the specific wavelength absorbed by a target gas and calculate the target gas concentration.

14 Claims, 4 Drawing Sheets

[Fig. 1]
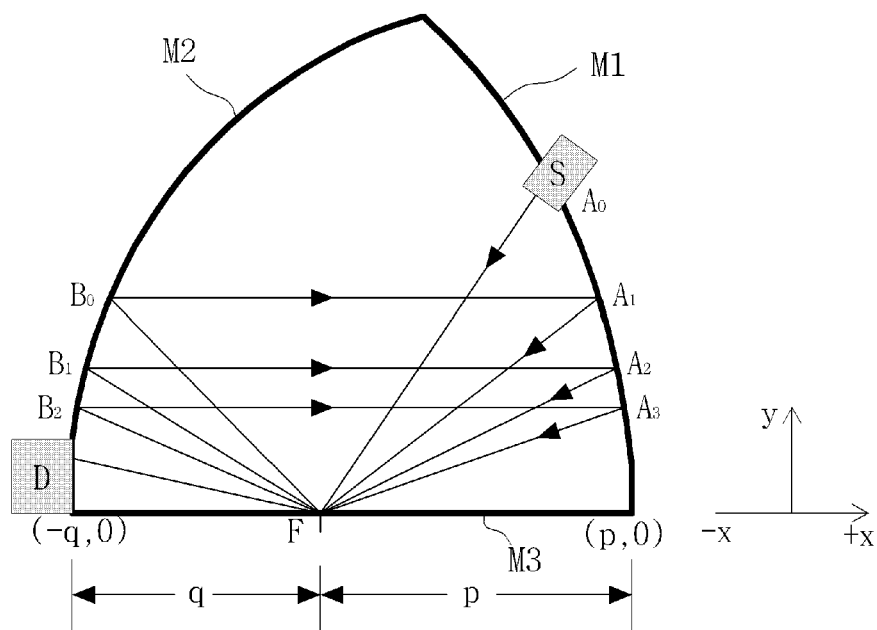
[Fig. 2]
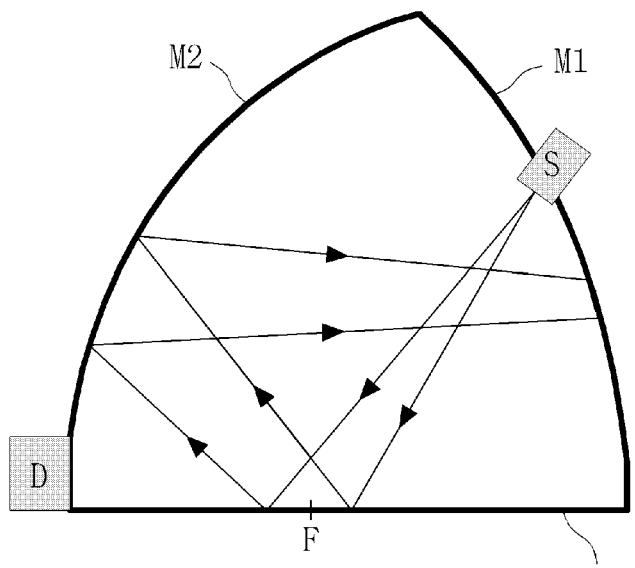
[Fig. 3]
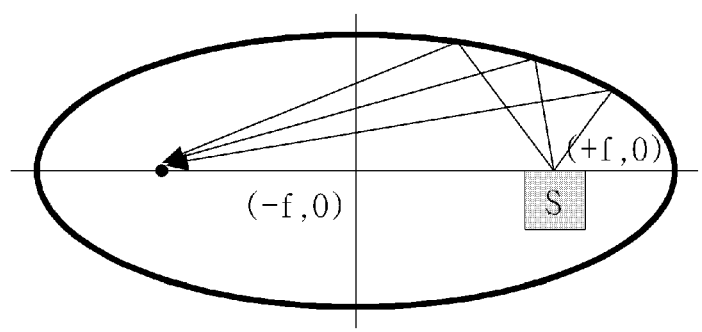

[Fig. 4]
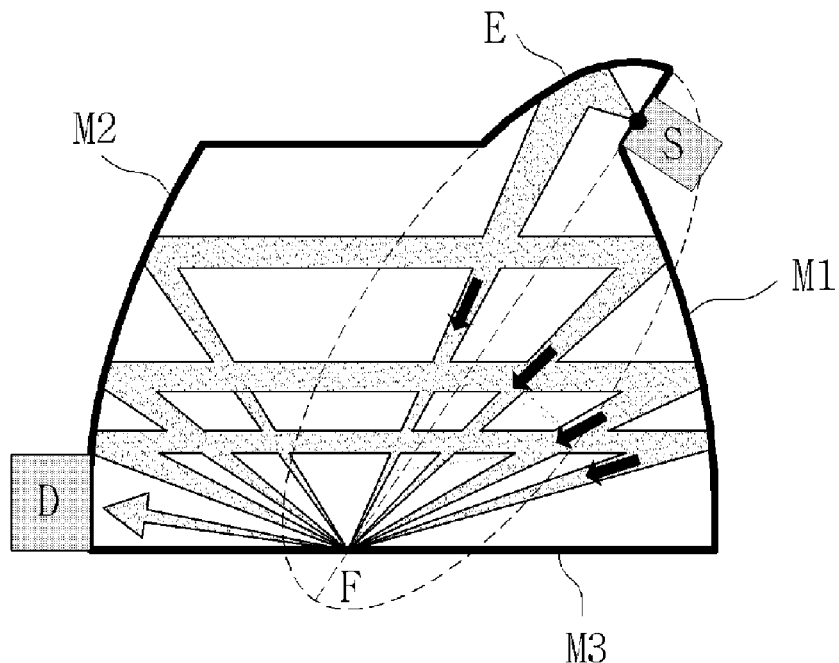
[Fig. 5]
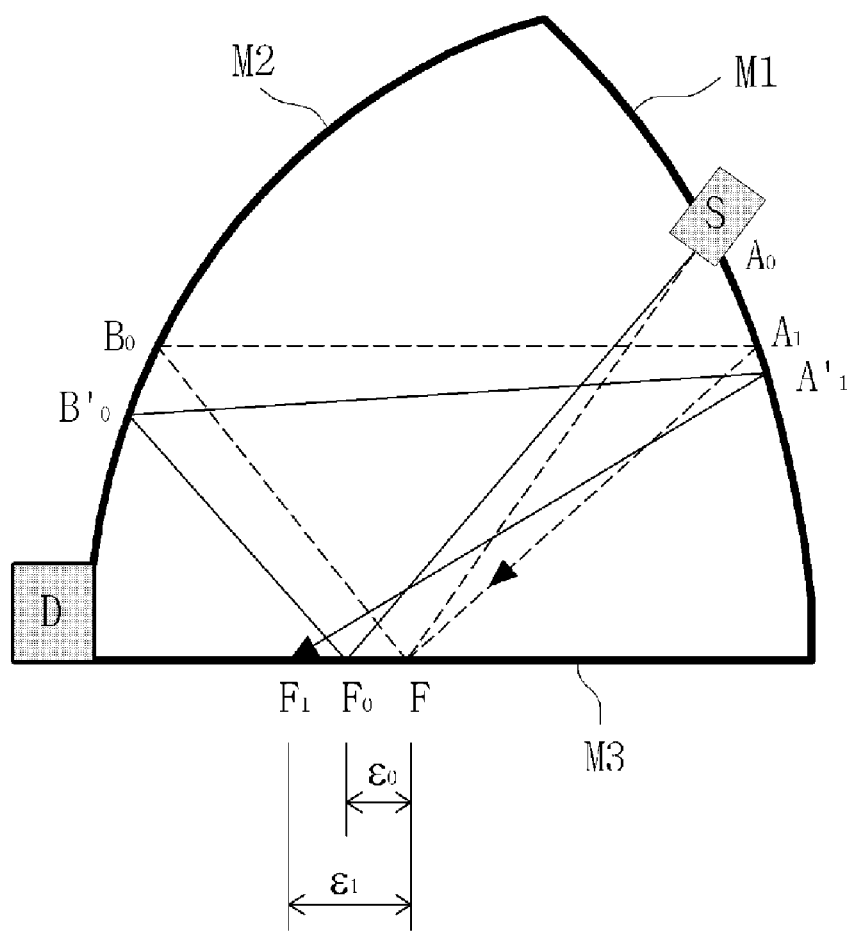

[Fig. 6]
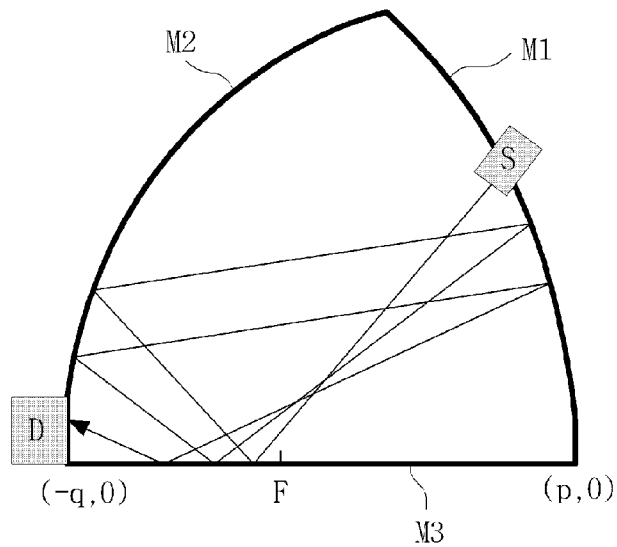
[Fig. 7]
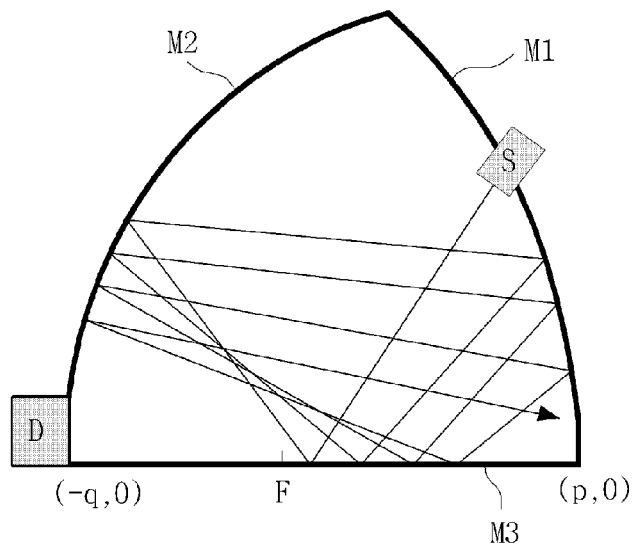
[Fig. 8]
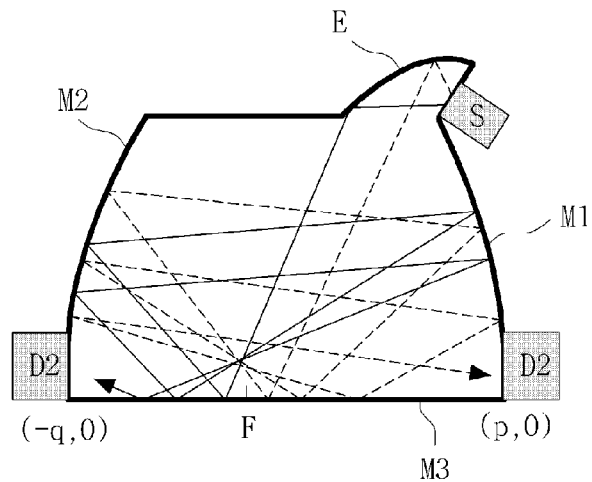

[Fig. 9]
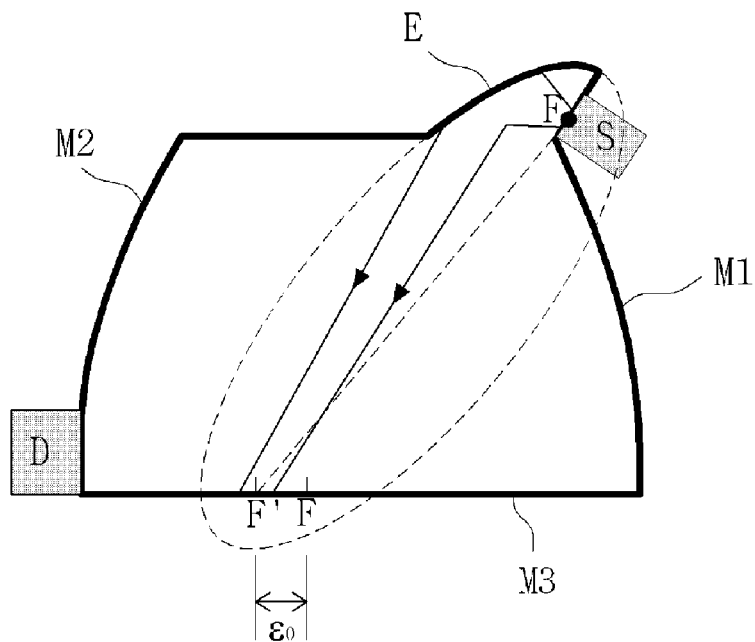
[Fig. 10]
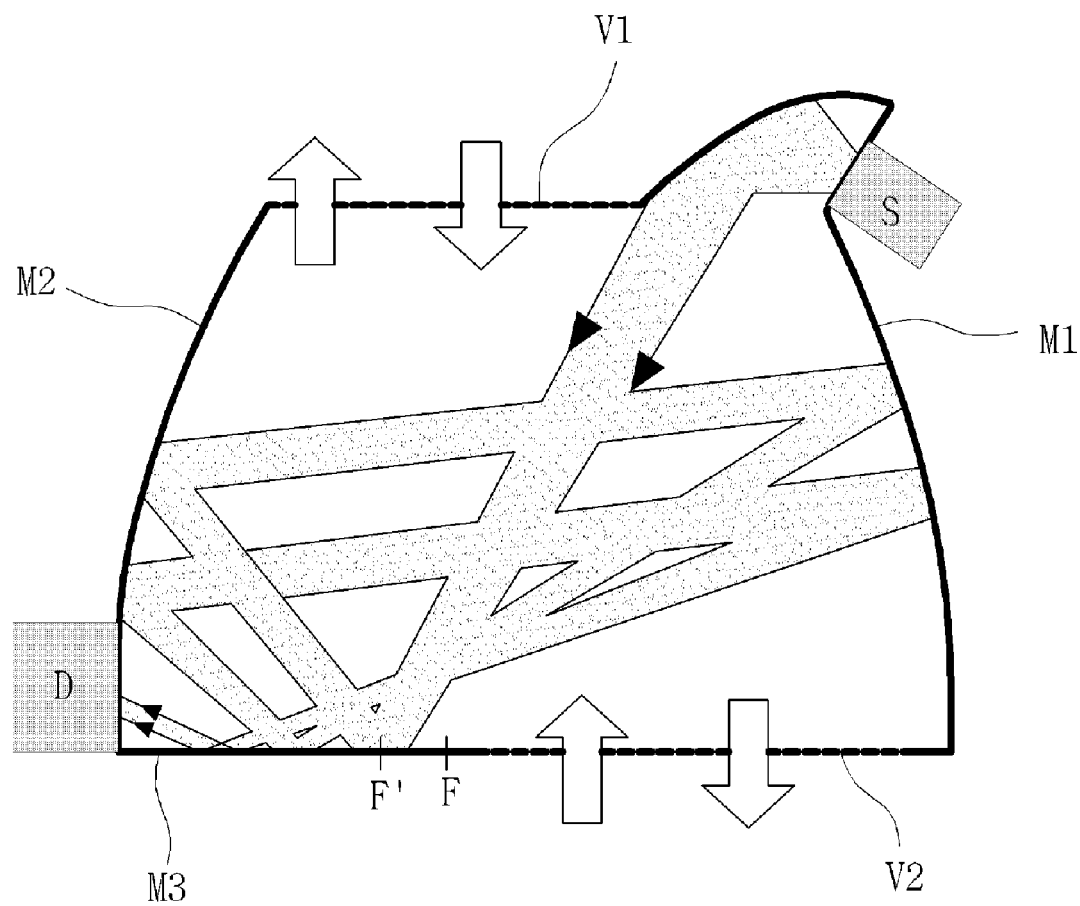

OPTICAL CAVITY FOR GAS SENSOR

BACKGROUND OF THE INVENTION

1. Field of the Invention

The present invention relates to an optical cavity for an Non-Dispersive Infrared (NDIR) gas sensor. More specifically, the sensors based on the principal of Non-Dispersive Infrared Detection uses the light-absorbing characteristic of gases to measure the amount of light absorption that occur at the specific wavelength that is absorbed by a target gas and calculate the target gas concentration.

2. Related Prior Art

An NDIR gas sensor normally comprises a gas chamber consisting of optical cavity, light source and light detector, and electronic circuits that analyze the electric signal from the light detector to get gas concentration.

In general, in order to obtain an NDIR gas sensor of superior quality with higher precision and accuracy, it is important to extend the length of the optical path within a given optical cavity so that the amount of absorbed light during the propagation of the light within the optical cavity increases.

However, simply increasing the optical cavity to get extended optical path may reduce the competitiveness of a product by causing an increase in the volume of the gas sensor and related manufacturing cost. One effective way of extending the optical path of an optical cavity of a limited size is to efficiently arrange the geometric position of mirrors and lenses in the optical cavity.

Due to the above-mentioned reason, it has been the most common way of designing and analyzing the conventional optical cavity to find the optimal geometric arrangement of the mirrors and lenses through trial and error using optical simulation technique. However, in the optical simulation, too many factors may affect the performance of the optical cavity and the accumulation of a number of small error factors occurring in the designing and manufacturing process of an optical cavity may result in a great deal of deviation in the performance of each product as well as a lot of time and cost consumption for the recovery of errors. Further, in designing an optical cavity using the optical simulation technique, one has to redesign the optical cavity by trial and error process in order to increase or decrease the length of the optical path with a given sized optical cavity and may obtain an impractical optical cavity that cannot be applied to a given gas sensor circuit.

In addition, in order to design an optical cavity of a high efficiency with a long optical path and a small cavity volume, the light radiated from a light source should be detected by a detector after sufficiently circulating inside the optical cavity to make the most use of the inner space of the given optical cavity. Under this situation, however, the space for gas ventilating opening shall be relatively reduced to cause the response time (i.e. time period required for one time measurement) to be excessively extended. That is, it might take several minutes to measure the gas concentration one time and thus the conventional gas cavity with a small space for gas ventilating opening could not be used in a sensing environment requiring a rapid measuring speed (or a short response time).

Still further, when measuring a gas having a good absorption characteristic to a thermal infrared using the NDIR detection (i.e. when measuring $CO_2$ gas that absorbs 4.2 micrometer infrared) the thermal infrared causes thermal vibration of the cavity material and thereby increases the temperature of the optical cavity. For example, when a light beam having energy of 100 is radiated from the light source a greater energy of more than 100 can be formed due to the temperature rise in the optical cavity, which results in the measurement error. In order to minimize this measurement error one may use pulse type light beam. However, efficient gas measurement may not be possible due to the small intensity of radiation at the light detector with a pulse type light beam of a small pulse width. In contrast, the use of a pulse type light beam of a large pulse width may affect the temperature rise inside the optical cavity and thus cause to incur the measurement error of the gas sensor.

Still further, since the characteristic of optical cavity including the length of optical path may be affected by various factors it is not easy to modify the design variables by repeated experiment after designing an optical cavity or to predict the characteristic change of the optical cavity and reflect the change onto the cavity design.

Since the light beam radiated from the light source has a predetermined beam width or beam size it is not possible to make all the radiated light to have an ideal optical path passing through a light focus. Therefore, it is very hard to design an optical cavity in consideration of the various optical paths that arise inside the optical cavity.

The above-mentioned problem prohibits the practical use of the NDIR gas sensor while it has a number of advantages compared to conventional gas sensors of other types.

SUMMARY OF THE INVENTION

The object of the present invention is to provide an optical cavity having both the extended optical path and the efficient ventilation characteristics.

Other object of the present invention is to effectively design the optical cavity that is an essential component of an NDIR gas sensor to have an extended optical path to get an increase in the measurement precision and accuracy, and to have a substantially increased ventilating opening size to facilitate the in and out of the target gas through the optical cavity thereby decreasing the response time required for measuring the gas concentration one time.

Another object of the present invention is to provide an optical cavity having a geometrically effective mirror arrangement ensuring a kind of contradictive target of having an extended optical path as well as an enlarged ventilating opening at the same time.

Another object of the present invention is to provide an optical cavity having a ventilating opening of a great size for facilitating the thermal radiation through the ventilating opening to prevent the measurement error due to the temperature rise within the optical cavity.

Another object of the present invention is to provide an optical cavity that is capable of facilitating the gas inflow and outflow and preventing the temperature rise within the optical cavity due to unnecessary optical paths having many light reflections that are not detected by the light detector by inducing the radiated light to be reflected at a predetermined section on the plane mirror and employing the ventilating opening in other section of the plane mirror without the light reflection.

Another object of the present invention is to provide an optical cavity having an effective light detection characteristic by arranging the mirrors of the optical cavity as a convergence system and positioning the light detector to a convergence point of the convergence system.

Another object of the present invention is to provide an optical cavity that enables the cavity designers to design the cavity with a simple geometric figure than can be easily analyzed and to easily change the optical path by changing a minimum number of cavity design factors thereby reducing the trial and error and cost for designing the optical cavity.

Another object of the present invention is to provide an optical cavity of which the optical path can be easily adjusted by controlling the ratio of focal distances of two quadratic parabolic mirrors and that is easy to be designed based on the applied gas type.

Another object of the present invention is to provide an optical cavity that is capable of conversance the radiated light having an expanded light beam size from its original state by reflecting the light to pass through a predetermined focus.

BRIEF DESCRIPTION OF THE DRAWINGS

FIG. 1 shows a schematic view showing the principle of an optical cavity according to the present invention.

FIG. 2 shows the propagation of light of which the beam size is spread out from that of the light at the light source.

FIG. 3 shows an optical reflection characteristic of light in the ellipsoidal mirrors.

FIG. 4 shows an optical cavity of the present invention employing an ellipsoidal mirror.

FIG. 5 shows the optical path of light incident to the focal point with slight deviations.

FIG. 6 shows the optical path of the light incident to the focal point with a deviation to the −x axis direction.

FIG. 7 shows the optical path of the light incident to the focal point with a deviation to the +x axis direction.

FIG. 8 shows an optical cavity using two light detectors.

FIG. 9 shows an optical cavity with the focus of the ellipsoidal mirror moved to the −x axis direction.

FIG. 10 shows an optical cavity with the ventilating opening.

DETAILED DESCRIPTION OF THE INVENTION

For the aforesaid object, the optical cavity according to one aspect of the present invention comprises two oppositely arranged parabolic mirrors having common focus located on the common optical axis of the parabolic mirrors; and a plane mirror arranged along the optical axis between the vertexes of each of the parabolic mirrors.

In the above-mentioned optical cavity, the light radiated from an arbitrary point on the parabolic mirror having longer focal distance circulates the inside of the optical cavity, goes along the optical axis to the positive and negative directions, and finally converges into the optical axis. Therefore, a light detector located in parallel to the optical axis can detect all the lights radiated from the light source.

In the above-mentioned optical cavity, light reflection occurs only at the focal point of the parabolic mirrors on the plane mirror. Since light reflection occurs only at the focal point located on the plane mirror the light does not reflects from the remaining parts of the plane mirror. Therefore ventilating opening can be located on the remaining parts of the plane mirror where the reflection does not occur.

According to the present invention, one can design an optical cavity having a substantially long optical path of a convergence system and a substantially large ventilating opening using two quadratic parabolic mirrors having a different focal distances and a plane mirror between them.

The optical cavity according to the above-mentioned structure has a characteristic of adjusting the length of the optical paths by changing the ratio of focal distances of the two parabolic mirrors. According to the principle of parabola, an infinite length of optical path can be formed when the ratio of focal distances of the two parabolic mirrors is 1:1. When the ratio is set to 1:n, one can easily design the optical cavity according to the applied gas type by shortening the length of optical path by decreasing the value of "n" for a gas of higher absorptive or extending the length by increasing the value of "n" for a gas of lower absorptive.

Ideally all the radiated light beams arrive at the focus on the optical axis. However practical light beams radiated from the light source having a predetermined beam width or beam size cannot arrive at the one focal point as proposed by the ideal optical path. Therefore, an optical cavity should be designed so that the radiated light beam having the predetermined beam size or deviated from its original optical path can converge into the focal point and then finally converge into the light detector.

Embodiments of the present invention will now be described with reference to the accompanied drawings.

1. Propagation of Light from an Ideal Light Source within an Optical Cavity

FIG. 1 shows a schematic view showing the principle of an optical cavity according to the present invention.

As shown in the FIG. 1 the optical cavity of the present invention basically comprises two quadratic parabolic mirrors (M1, M2) and one plane mirror (M3).

The one parabolic mirror M1 having focal distance p can be described as the following equation (1) and the other parabolic mirror M2 having focal distance q can be described as the following equation (2).

$$M1: y^2 = -4p(x-p) \quad (1)$$

$$M2: y^2 = 4q(x+q) \quad (2)$$

Both equations (1) and (2) describe parabolas having a common focus at the origin of coordinates and a common optical axis in the x axis of coordinates. For explanation purposes, the x axis of x, y, z coordinates are hereby taken as the optical axis, a reference axis for optical analysis.

In general, a quadratic parabola of the equation, $y^2=4p(x-p)$, has its focus at (p, 0) and has x axial symmetry. Based on the reflection characteristics of a quadratic parabolic mirrors, an incident light in parallel to the optical axis (x axis) reflects from the quadratic parabolic mirror to pass the focus (p, 0) and an incident light passing through the focus (p, 0) reflects from the quadratic parabolic mirror to travel in parallel to the optical axis (x axis).

Using the above characteristics of the quadratic parabolic mirrors, two quadratic parabolic mirrors (M1, M2) having focal distances of p and q (p>q), respectively, are arranged in opposition to each other to have a common focus (F) located on the common optical axis (x axis) of the parabolic mirrors, a plane mirror (M3) is arranged along the optical axis (x axis), and a light detector (D) is located on the one end of the optical axis. A light radiated from the light source (S) at point (A0) to the focus (F) on the optical axis reflects from the focus (F) and then circulates the cavity with an optical path of B0→A1→F→B1→A2 ... →D. The focal distances "p" and "q" should satisfy a condition of p>q. If p=q then the radiated light will not converge into the detector (D) and will have infinite circulation. For the light to converge into the detector (D), the light source (S) should be on the parabolic mirror (M1) having a focal distance p (p>q). The light will converge into the optical axis (x axis) even when the light source (S) is located at any arbitrary point on the parabolic mirror (M1).

When the coordinates of reflection points are given as $A0=(\alpha 0, \beta 0)$, $An=(\alpha n, \beta n)$, $B0=(\alpha 0', \beta 0')$, $Bn=(\alpha n', \beta n')$, the points An and Bn can be expressed as equation (3) from the equations (1) and (2) and a condition of $\beta 0'=\beta 1$.

$$A_0 = (\alpha_0, \beta_0) \tag{3}$$

$$B_0 = (\alpha'_0, \beta'_0) = \left(-\frac{q}{p}\alpha_0, \frac{q}{p}\beta_0\right)$$

$$A_n = (\alpha_n, \beta_n) = \left(\left(\frac{q}{p}\right)^{2n}(\alpha_0 - p) + p, \left(\frac{q}{p}\right)^n \beta_0\right)$$

$$B_n = (\alpha'_n, \beta'_n) = \left(-\left(\frac{q}{p}\right)^{2n+1}(\alpha_0 - p) - q, \left(\frac{q}{p}\right)^{n+1} \beta_0\right)$$

From the equation (3), if $n \to \infty$ then $\alpha_n \to p$, $\alpha_n' \to -q$, and $\beta_n = \beta_n' \to 0$. As the number of circulation increases the light converges along the optical axis to be eventually detected by the light detector (D) on the optical axis.

The light radiated from the light source (S) circulates the optical cavity a predetermined times N to be detected by the light detector (D) located at the point (−q, 0) on the optical axis. When the ratio of the diameter of the light detector (D) (i.e., the dimension of the light detector (D) in the y axis) to the focal distance p is m (m<1) (i.e., the size of the light detector=mp) then the number of circulation N is given as below equation (4).

From equation (3) and the condition $B_N < mp$, the equation (4) explaining the condition that the light converges into the light detector (D) after N times of circulation is induced.

$$B_N = \left(\frac{q}{p}\right)^{N+1} \beta_0 < mp \tag{4}$$

$$N > \frac{\ln\left(\frac{mp^2}{q\beta_0}\right)}{\ln\left(\frac{q}{p}\right)}$$

For example, if p=20 mm, q=16 mm, m=0.2, the size of light detector=0.2p=4 mm, and $\beta_0$=20 mm then N>6.21 from the equation (4), which means that the light radiated from the light source (S) is detected by the light detector (D) in its seventh circulation after six times of circulation in the optical cavity.

Meanwhile the total length of the optical path from the light source (S) to the detector (D) can be induced by a generalization of the length of the nth circulation. $L_n$, the length of the nth circulation, is given as the equation (3) based on the FIG. 1.

$$L_n = \overline{A_{n-1}F} + \overline{FB_{n-1}} + \overline{B_{n-1}A_n} \tag{5}$$

$$= \sqrt{\alpha_{n-1}^2 + \beta_{n-1}^2} + \sqrt{\alpha_{n-1}'^2 + \beta_{n-1}'^2} + (\alpha_n - \alpha_{n-1})$$

$$= 2p - \alpha_{n-1} + 2q + \alpha_{n-1}' + \alpha_n - \alpha_{n-1}'$$

$$= 2(p+q) + \alpha_n - \alpha_{n-1}$$

$$= 2(p+q) + \left(\frac{q}{p}\right)^{2n-2}\left(\left(\frac{q}{p}\right)^2 - 1\right)(\alpha_0 - p)$$

When the light detector (D) detects the light radiated from the light source (S) after N time of circulation the total length of the optical path for N times of circulation is given as $$L = \sum_{n=1}^{N} L_n = \sum_{n=1}^{N}\left[2(p+q) + \left(\frac{q}{p}\right)^{2n-2}\left(\left(\frac{q}{p}\right)^2 - 1\right)(\alpha_0 - p)\right] \tag{6}$$

$$= 2N(p+q) + \left(1 - \left(\frac{q}{p}\right)^{2N}\right)(p - \alpha_0)$$

For example, if p=20 mm, q=16 mm, m=0.2, the size of light detector=0.2p=4 mm, $\beta_0$=20 mm, and $\alpha_0$=15 mm then N=7 from equation (4). However since the seventh circulation was incomplete by the amount of $\alpha_N - \alpha_{N-1}'$ the total length of the optical path is given from the equation (6) as follows $$L(N=7) = 2N(p+q) + \left(1 - \left(\frac{q}{p}\right)^{2N}\right)(p - \alpha_0) - (\alpha_N - \alpha_{N-1}') \tag{7}$$

$$= 2N(p+q) + \left(1 - \left(\frac{q}{p}\right)^{2N}\right)(p - \alpha_0) -$$

$$\left(\frac{q}{p}\right)^{2N}(\alpha_0 - p) - p - \left(\frac{q}{p}\right)^{2N-1}(\alpha_0 - p) - q$$

$$= (2N-1)(p+q) + (p - \alpha_0)\left(1 + \left(\frac{q}{p}\right)^{2N-1}\right)$$

Substitution of the above given number to the equation (7) results in the total length of optical path L≈473 mm.

Meanwhile, in the optical cavity of a gas sensor according to the present invention, the optical path can be adjusted by controlling the focal distances (p, q) of the parabolic mirrors (M1, M2). That is, the length of the optical path can be adjusted by controlling the ratio between the focal distances p and q in the equation (7) according to the application of the optical cavity. For example, the optical path can be designed to be short for a gas of higher light absorptive such as carbon dioxide, while the optical path can be designed to be long by adjusting the values of p and q for a gas of lower light absorptive such as carbon monoxide.

2. Design of Optical Cavity for a Light Source having Diffusive Characteristics

Generally lights radiated from a commercially available normal light source have diffusive characteristics. That is, the light source is not a point source of light and the light of a certain size is radiated with a certain degree of diffusion. So the light path from the normal light source is not given as in FIG. 1. Rather it is given as in FIG. 2.

FIG. 2 shows the propagation of light of which the beam size is spread out from that of the light at the light source.

In FIG. 2, not all the lights radiated from the light source (S) converge into the focus (F). The lights spread for a certain width to the +x and −x axis direction with reference to the focus (F) due to the diffusive characteristic of light. The optical path for the light spreading into the +x axis is different from that for the light spreading into the −x axis, and parts of the light beam may not be detected by the light detector (D). In the present invention, an ellipsoidal mirror is used to converge the diffusive light into the focus (F).

FIG. 3 shows an optical reflection characteristic of light in the ellipsoidal mirrors.

According to the principle of an ellipsoid, the light radiated from a light source located at one focus of the ellipsoid will converge into the other focus after reflecting from the ellipsoidal mirror. An optical cavity structure according to one embodiment of the present invention employing the ellipsoidal mirror is shown in FIG. 4.

FIG. 4 shows an optical cavity of the present invention employing an ellipsoidal mirror.

In FIG. 4, the light source (S) is on one focus (f) f the ellipsoidal mirror (E). The other focus of the ellipsoidal mirror (E) is the common focus (F) of the two parabolic mirrors (M1, M2). All the lights radiated from the focus (f) of the ellipsoid (E) reflect from the surfaces of the ellipsoid mirror (E) and then converge into the common focus (F) of the two parabolic mirrors (M1, M2). This convergent light will eventually converge into the light detector (D) according to the reflection characteristic of the two parabolic mirrors (M1, M2).

3. Design of Optical Cavity for Deviated Optical Path

The optical cavity of FIG. 4 was designed to converge most of the light within the optical cavity into the optical detector (D) by focusing the diffusive light from the light source (S) into the common focus (F) using the ellipsoidal mirror (E). However in the practical optical cavity made from the above design they may exist a light path that deviates from the focus. Therefore it is necessary to design the optical cavity so that all the lights may have light paths converging into the light detector (D).

FIG. 5 shows the optical path of light incident to the focal point with slight deviations.

In FIG. 5, the optical path indicated as dotted line represents an ideal case where the radiated light exactly converges into the focus (F), while the optical path indicated as solid line represents a case where whole or part of the radiated light deviates from the focus (F).

Let $\epsilon 0$ be the amount of deviation of light from the focus (F) when the light radiated from the light source (S) arrives at the optical axis, $$\frac{\varepsilon_0}{p}, \frac{\varepsilon_0}{q}, \frac{\varepsilon_0}{\alpha_0}, \frac{\varepsilon_0}{\beta_0} \ll 1,$$

and square values of them approximate to zero.

Let the ideal optical path be $A0 \to F \to B0 \to A1$ and the deviated optical path deviating the focus (F) by $\epsilon 0$ be $A0 \to F0 \to B0' \to A1'$. With reference to the equation (3), the coordinates of reflecting points in the deviated optical path can be described as $$A_0 = (\alpha_0, \beta_0)$$

$$B_0 = (\alpha_0', \beta_0') = (-T\alpha_0, T\beta_0)$$

$$B_0' = (\alpha_0' + \mu_0, \beta_0' + \nu_0) = (-T\alpha_0 + \mu_0, T\beta_0 + \nu_0)$$

$$A_1 = (\alpha_1, \beta_1) = (T^2(\alpha_0 - p) + p, T\beta_0)$$

$$A_1' = (\alpha_1 + \gamma_1, \beta_1 + \delta_1) = (T^2(\alpha_0 - p) + p + \gamma_1, T\beta_0 + \delta_1)$$

$$F_0 = (\epsilon_0, 0)$$

$$F_1 = (\epsilon_1, 0) \quad (8)$$

The values of $\mu_0, \nu_0, \gamma_1, \delta_1$ are very smaller than p like the value of $\epsilon_0$. So the square values of $$\frac{\mu_0}{p}, \frac{\nu_0}{p}, \frac{\gamma_1}{p}, \frac{\delta_1}{p}$$

and their multiplications approximate to zero. Let us get the value of A1 from the deviated optical path and generalize. The light radiated from A0 reflects from the point F0 which deviates from the focus (F) and arrives at point B0'. Since $\overline{B0'}$ is a point on the parabolic mirror (M2) and the slope of $\overline{A_0 F_1}$ is opposite to the slope of $\overline{F_0 B_0}$, the coordinates of B0' is given from $$(\beta_0' + \nu_0)^2 = 4q(\alpha_0' + \mu_0 + q) \quad (9)$$

$$\frac{\beta_0' + \nu_0}{\alpha_0' + \mu_0 - \epsilon_0} = -\frac{\beta_0}{\alpha_0 - \epsilon_0} \quad (10)$$

Solving the equations (9) and (10) with respect to $\mu_0$ and $\nu_0$ gives the following equation.

$$\mu_0 = \frac{2(T+1)(p - \alpha_0)}{2p - \alpha_0} \epsilon_0 \quad (11)$$

$$\nu_0 = \frac{\beta_0(T+1)}{2p - \alpha_0} \epsilon_0 \quad (12)$$

where $T = \frac{q}{p}, (0 < T < 1)$.

The coordinates of A1' can also be calculated from the laws of light reflection and the laws of subtraction in a trigonometric function. That is, with reference to the normal line at the point B0' the magnitude of the incident angle $\overline{F_0 B_0'}$ is equal to that of the reflection angle $\overline{B_0' A_1'}$. Therefore tan $(\overline{B_0' A_1'})$, the slope of $\overline{B_0' A_1'}$, is calculated from the equation (13).

$$\tan(\overline{B_0' A_1'}) = -\frac{\beta_0}{T(2p - \alpha_0)^2} \epsilon_0 \quad (13)$$

The coordinates of A1' is given by the equation (13) and the laws of reflection as the equation (14).

$$A_1' = (\alpha_1 + \gamma_1, \beta_1 + \delta_1) = (T^2(\alpha_0 - p) + p + \gamma_1, T\beta_0 + \delta_1) \quad (14)$$

$$\gamma_1 = -\frac{2(p - \alpha_0)(T+1)(3pT - 2T\alpha_0 - p)}{(2p - \alpha_0)^2} \epsilon_0$$

$$\delta_1 = \frac{\beta_0(T+1)(3pT - 2T\alpha_0 - p)}{T(2p - \alpha_0)^2} \epsilon_0$$

The light reflected from the point A1' reaches the optical axis again at point $F1 = (\epsilon 1, 0)$. $\epsilon 1$ can be induced from the equation (15) using the laws of light reflection at point A1 and the laws of subtraction in a trigonometric function.

$$\epsilon_1 = H^2 \epsilon_0 = \left[\frac{p + T^2(p - \alpha_0)}{T(2p - \alpha_0)}\right]^2 \epsilon_0 \quad (15)$$

As shown in the equation (15), $\epsilon 1$ and $\epsilon 0$ have the same sign.

The same sign denotes that when the deviated light arrives at the −x axis the reflected light will arrive at the same −x axis after circulating the cavity, whereas when the deviated light arrives at the +x axis the reflected light will arrive at the same +axis after circulating the cavity. That is, when deviated lights are divided into lights of positive direction and lights of negative direction with respect to the focus F (0, 0), all the reflection points on the optical axis of the negatively directed lights shall remain on the negative direction from the focus (F) as shown in FIG. 6, and all the reflection points on the optical axis of the positively directed lights shall remain on the positive direction from the focus (F) as shown in FIG. 7.

In the end, the negatively deviated lights can reach the light detector (D) as shown in FIG. 6, whereas the positively deviated lights cannot reach the light detector (D) as shown in FIG. 7.

4. Correction of Deviated Optical Path

As shown in FIGS. 6 and 7, the light incident to the focus (F) with deviation shall divide into (+) and (−) directions to have different optical path from each other.

FIG. 8 shows an optical cavity using two light detectors.

When light detectors (D1, D2) are located at points (−q, 0) and (p, 0), respectively as shown in FIG. 8, most of the lights radiated from the light source (S) can be detected and the efficiency of the gas sensor will be maximized. That is, among the lights radiated from the light source (S), the lights that arrived at the optical axis to the −x direction will have an optical path indicated as the solid line and will be detected by the light detector (D1) on the left-hand side of the optical axis, and the lights that arrived at the optical axis to the +x directions will have a different optical path indicated as the dotted line and will be detected by the light detector (D2) on the right-hand side of the optical axis. Therefore the two detectors will detect most of the lights radiated from the light source and thus the efficiency of detection will be maximized.

However, while the precision and accuracy of the gas sensor can be increased by the maximization of the use of light in the optical cavity in FIG. 8, there is a limitation in the arrangement of ventilating openings because no ventilating opening can be provided on the optical axis.

Meanwhile it is not possible to practically radiate the light from the light source (S) so that all the lights exactly converge into the focus (F) even when forcibly converging the radiated lights into the focus (F) using the ellipsoidal mirror (E) as shown in FIG. 5, and the light shall be divided into (+) and (−) direction centering on the focus (F) to cause the inevitable loss of light corresponding to half the total light when only one light detector is located at point (−q, 0) or (+q, 0). This loss of light can be minimized by arranging the light source (S) and/or the ellipsoidal mirror (E) as shown in FIG. 9.

FIG. 9 shows an optical cavity with the focus of the ellipsoidal mirror moved to the −x axis direction.

FIG. 9 illustrates the optical cavity structure wherein the focus (F') of the ellipsoidal mirror (E) is slightly moved to the +x axis from the common focus (F) of the parabolic mirrors (M1, M2).

As shown in FIG. 9, one of the two focuses (f, F') of the ellipsoidal mirror (E) is located on the light source (S) while the other is located at a point (F') which is slightly moved from the common focus (F) of the parabolic mirrors (M1, M2) toward the −x axis by an amount of ϵ0. The distance ϵ0 between the focus of the parabolic mirror (M1, M2) and the focus of the ellipsoidal mirror (E) will vary depending upon the effectiveness in the performance of ellipsoidal mirror (E) for concentrating the lights.

In FIG. 9, if most of the lights radiated from the optical source (S) are incident into the optical axis in the −x direction in respect to the common focus (F) on the plane mirror (M3) then these lights will eventually be detected by the light detector (D). Since no lights are reflected on the optical axis in the +x direction in respect to the common focus (F) on the plane mirror (M3) ventilating openings can be provided in this part of the plane mirror (M3). The structure of optical cavity having the ventilating opening is shown in FIG. 10.

FIG. 10 shows the structure of an optical cavity with the ventilating opening and the optical path within the optical cavity.

FIG. 10 shows the optical cavity wherein the ventilating openings are provided in the parts of the plane mirror where no optical path exists. That is, since the light radiated from the optical source (S) gradually converges into the light detector (D) located on the optical axis without touching the upper plane mirror conjoining the ellipsoidal mirror (E) and the light source (S), ventilating openings (V1) may be located in the upper plane mirror. Further, if the reflection points are confined to the −x direction in respect to the common focus (F) by setting the focus of the ellipsoidal mirror (E) to the point (F') slightly spaced from the common focus (F) then another ventilating openings (V2) may be located in the +x direction of the optical axis wherein no reflection of lights occur.

Since these arrangements of ventilating openings become possible not because of the existence of the ellipsoidal mirror (E) but because of setting the incident points of the lights radiated from the light source (S) to the point (F') which is slightly spaced from the common focus (F) on the plane mirror (M3), the same results can be obtained even without the ellipsoidal mirror (E) as long as the radiating angle of lights from the light source (S) is designed to meet the above-identified conditions.

The ventilating openings (V1, V2) can be a number of ventilating holes formed on the plane mirrors as shown in FIG. 10, or they can be in the form of cutout in a part of the plane mirrors. There is no limit in the form of the ventilating openings as long as they functions to inflow and outflow the gases to be detected. In addition, a filter (not shown) for filtering out dust and particles during ventilation can be provided to the ventilating openings (V1, V2).

Since no light passes or reflects on the ventilating openings (V1, V2) no loss of light occur due to the existence of them. The response time of gas sensor can be reduced by maximizing the size of the ventilating openings to facilitate the flow of gases to be tested. That is, the important factor in designing the ventilating openings (V1, V2) is not the specific position of them but a principle that the ventilating openings are provided in the optical cavity wherein no reflection of light occurs. For example, the ventilating openings may be provided in the top and bottom surfaces that are perpendicular to the sidewalls consisting of the mirrors (M1, M2, M3).

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

According to the present invention, an optical cavity for an NDIR gas sensor having both the extended optical path and the efficient ventilation characteristics is provided.

Since the optical cavity according to the present invention is an optical convergence system for the optical path using two parabolic mirrors and a plane mirror wherein the reflection of lights occurs only in the predetermined area within the optical cavity and the ventilation of gas facilitates due to the ventilating openings provided in a certain area within the optical cavity where no reflection of lights occur, the convergence system with an extended light path gives a feature of light focusing function and the efficient ventilation characteristics gives a feature of fast response function to the optical cavity.

The optical cavity according to the present invention has an extended optical path for increasing the measurement precision and accuracy and a substantially increased ventilating opening size for facilitating the inflow and outflow of the target gas through the optical cavity thereby decreasing the response time required for measuring the gas concentration.

The optical cavity according to the present invention has a geometrically effective mirror arrangement ensuring a kind of contradictive target of having an extended optical path as well as an enlarged ventilating opening at the same time.

The optical cavity according to the present invention has a ventilating opening of a great size to facilitate the thermal radiation for preventing the measurement error due to the temperature rise within the optical cavity.

The optical cavity according to the present invention is capable of facilitating the gas inflow and outflow through the increased gas ventilating opening and preventing the temperature rise within the optical cavity due to unnecessary optical paths having many light reflections that are not detected by the light detector by inducing the radiated light to be reflected at a predetermined section on the plane mirror and employing the ventilating opening in other section of the plane mirror without the light reflection.

The optical cavity of the present invention has an effective light detection characteristic by arranging the mirrors of the optical cavity as a convergence system and positioning the light detector to a convergence point of the convergence system.

The optical cavity design of the present invention enables the cavity designers to design the optical cavity with a simple geometric figure that can be easily analyzed. Using the optical cavity design of the present invention, one can easily change the optical path by changing a minimum number of cavity design factors thereby reducing the trial and error and cost for designing the optical cavity.

In the optical cavity according to the present invention, the optical path can be easily adjusted by controlling the ratio of focal distances of two quadratic parabolic mirrors and different optical path can be easily designed based on the applied gas type.

The optical cavity according to the present invention is capable of converging the radiated light having an expanded light beam size from its original state by reflecting the light to pass through a predetermined focus.

According to the present invention, the design or structure of optical cavity can be reduced to mathematical expression or numerical formulas for providing a simple method for designing and analyzing different optical cavities and thus the time and cost for designing and producing the optical cavity can be substantially reduced in comparison to the method using conventional optical simulation.

The new optical cavity structure according to the present invention can be used for an NDIR gas sensor that is widely used for air quality control purposes including indoor air quality control, HVAC (Heating, Ventilating and Air-Conditioning) system for vehicles, etc.

The invention claimed is:

1. An optical cavity for gas sensor comprising:
   a first parabolic mirror having a first focal distance;
   a second parabolic mirror having a second focal distance that is greater than the first focal distance and the second parabolic mirror being oppositely arranged to the first parabolic mirror; and
   a plane mirror arranged between one end of the first parabolic mirror and one end of the second parabolic mirror, wherein the two oppositely arranged parabolic mirrors have common focus located on the common optical axis of the parabolic mirrors, the plane mirror is arranged along the optical axis, and the common focus lies on the surface of the plane mirror.

2. The optical cavity according to claim 1 further comprising: a light source located on the side of the second parabolic mirror for radiating lights to the plane mirror arranged along the optical axis; and a light detector located at the connecting point of the first parabolic mirror and the plane mirror for detecting the light that has been reflected within the optical cavity by the first parabolic mirror, the second parabolic mirror and the plane mirror one after another.

3. The optical cavity according to claim 2, wherein the angle of radiation of the lights from the light source is set so that the lights from the lights source are incident into the plane mirror portion between the light detector and the common focus.

4. The optical cavity according to claim 3, wherein the incident point of the light on the plane mirror portion is adjusted between the light detector and the common focus and the length of the optical path within the optical cavity is also adjusted depending on the angle of radiation of the lights from the light source.

5. The optical cavity according to claims 4, further comprising gas ventilating openings provided in a predetermined part of the optical cavity where no reflection of light occurs.

6. The optical cavity according to claim 5, wherein the gas ventilating openings are provided in a predetermined part of the optical cavity between the other end of the first parabolic mirror and the other end of the second parabolic mirror.

7. The optical cavity according to claim 5, wherein the gas ventilating openings are provided in a predetermined part of the optical cavity between the common focus and the one end of the second parabolic mirror.

8. An optical cavity for a gas sensor comprising:
   a top surface; a bottom surface; and sidewalls between the top surface and the bottom surface, wherein the sidewalls comprises a first surface, a second surface, a third surface, and a fourth surface in the clockwise direction,
   the first surface is formed by a first parabolic mirror having a first focal distance,
   the third surface is formed by a second parabolic mirror having a second focal distance that is greater than the first focal distance and the second parabolic mirror being oppositely arranged to the first parabolic mirror,
   the fourth surface is formed by a first plane mirror arranged between the lower end of the first parabolic mirror and the lower end of the second parabolic mirror, and
   the second surface is formed by a second plane mirror conjoining an ellipsoidal mirror, the second plane mirror being arranged between the upper end of the first parabolic mirror and one end of the ellipsoidal mirror and the ellipsoidal mirror being arranged between one end of the second plane mirror and the upper end of the second parabolic mirror.

9. The optical cavity according to claim 8, wherein the first parabolic mirror and the second parabolic mirror have common focus located on the common optical axis of the parabolic mirrors, the first plane mirror is arranged along the common optical axis, and the common focus is formed on the surface of the first plane mirror.

10. The optical cavity according to claim 9 further comprising:
- a light source located on the side of the second parabolic mirror for radiating lights to the first plane mirror arranged along the optical axis; and
- a light detector located at the connecting point of the first parabolic mirror and the first plane mirror for detecting the light that has been reflected within the optical cavity by the first parabolic mirror, the second parabolic mirror and the first plane mirror one after another.

11. An optical cavity according to claim 9, wherein the first parabolic mirror, the second parabolic mirror and the first plane mirror are arranged so that the optical path within the optical cavity can form a convergence system of light, and the light detector is arranged at the light converging point of the convergence system.

12. The optical cavity according to claim 11, wherein one focus of the ellipsoidal mirror is formed near the position of the common focus.

13. The optical cavity according to claim 11, further comprising gas ventilating openings provided in a predetermined part of the optical cavity where no reflection of light occurs.

14. The optical cavity according to claim 11, wherein the gas ventilating openings are provided in the top or bottom surface of the optical cavity.

* * * * *